United States Patent [19]
Knight et al.

[11] Patent Number: 5,830,359
[45] Date of Patent: Nov. 3, 1998

[54] METHOD OF SEPARATING PARTICLES FROM A FILTER

[75] Inventors: Jan Knight; Robert Knight, both of Plymouth, United Kingdom

[73] Assignee: Knight Scientific Limited, Plymouth, United Kingdom

[21] Appl. No.: 530,221

[22] PCT Filed: Apr. 7, 1994

[86] PCT No.: PCT/GB94/00774

§ 371 Date: Oct. 3, 1995

§ 102(e) Date: Oct. 3, 1995

[87] PCT Pub. No.: WO94/23296

PCT Pub. Date: Oct. 13, 1994

[30] Foreign Application Priority Data

Apr. 7, 1993 [GB] United Kingdom .................. 9307321

[51] Int. Cl.⁶ .................................................. B01D 61/00
[52] U.S. Cl. .......................... 210/651; 210/662; 210/772; 210/782; 210/785; 210/787; 210/321.69; 210/500.21; 356/39; 422/101; 436/178
[58] Field of Search ............................... 210/691, 321.69, 210/651, 767, 662, 772, 348, 500.1, 782, 785, 500.21, 787, 512.1, 791; 356/39; 422/101; 436/178; 604/4, 5

[56] References Cited

U.S. PATENT DOCUMENTS

| | | | |
|---|---|---|---|
| 4,330,410 | 5/1982 | Takenaka et al. | 210/767 |
| 5,240,613 | 8/1993 | Tsuchitani et al. | 210/785 |
| 5,252,228 | 10/1993 | Stokes et al. | 422/101 |

FOREIGN PATENT DOCUMENTS

| | | |
|---|---|---|
| 0 397 403 A1 | 11/1990 | European Pat. Off. . |
| 0 465 987 A2 | 1/1992 | European Pat. Off. . |
| 0 489 602 A2 | 6/1992 | European Pat. Off. . |

*Primary Examiner*—David A. Reifsnyder
*Attorney, Agent, or Firm*—Nixon & Vanderhye P.C.

[57] ABSTRACT

Particles that move at low Reynolds numbers are separated from a filter material on which they are adsorbed by subjecting the filter material, in a liquid medium, to agitation of sufficient magnitude to create turbulence and shear forces acting on the filter material such that the particles become desorbed from the filter material and become suspended in the liquid medium. The method may be used to recover biological particles, such as leucocytes and blood platelets, from filter materials on which they are retained by adsorption. The recovered particles may then be used in diagnostic testing and analytical techniques.

30 Claims, 2 Drawing Sheets

METHOD OF SEPARATING PARTICLES FROM A FILTER

BACKGROUND OF THE INVENTION

1. Field of the Invention

The invention relates to a method of separating particles from a filter material on which they are retained by adsorption and a method of recovering particles from fluids containing them. More particularly, the invention relates to a method for rapidly and selectively recovering biological particles, such as leucocytes and platelets, in a form in which they can be used for many different purposes.

2. Discussion of Prior Art

There are many fluids in which leucocytes may occur: whole blood, blood components, milk, colostrum, urine, tissue and tumour disaggregates and exudates, lymph, ascites fluid, cerebrospinal fluid, bile, peritoneal fluid, synovial fluid, seminal fluid, lacrimal fluid, interstitial fluid, hemolymph, saliva, tears, mantle fluid, bone marrow, coelomic fluid, glandular secretions, bronchoalveolar lavage, alveolar fluid, fluid from organs and tissues in culture, pathological discharges, discharges, mucus, pus and odematous fluid that accumulates in any space within a living organism.

Much information can be obtained from measuring, for example, the production by leucocytes of free radicals and other reactive oxygen containing species and of the enzymes produced and sometimes released by leucocytes when they become activated. These can be measured by adding a suitable luminogenic material, e.g., Pholasin (Registered Trade Mark), which will emit light in the presence of free radicals, certain oxidants, some reactive oxygen species and certain enzymes and any light emitted would be a measure of the activity of the leucocytes. Many other tests, including non-luminogenic tests are also performed on leucocytes. However, it is often essential if such tests are to be performed accurately, that the large majority of other cells, such as red blood cells, which may be present in the fluid from which the leucocytes were harvested are removed. It is also important in many cases to remove the plasma (or serum) and other fluid in which the leucocytes occur before carrying out many tests as components in the fluid may interfere with the performance of many tests.

One approach to the problem of potential interference from plasma components, such as complement, is to dilute a sample of whole blood at least 1:500. However, this procedure reduces at the same time the number of cells present in the sample by the dilution factor and, therefore, any measurable signal is also correspondingly reduced. As leucocytes, in whole blood, are in relatively small numbers compared to the red blood cells, any tests requiring large number of leucocytes isolated from red blood cells, or tests requiring the extraction of specific components from leucocytes, would still not be possible using samples of diluted whole blood.

There is a recurrent need selectively to separate biological particles, such as leucocytes or platelets, from blood, for example, for subsequent analysis. There is also a need selectively to separate leucocytes from other body fluids, for example seminal fluid, in order to obtain a pure sample of sperm which are to be used in subsequent fertility tests.

There are known methods for separating biological particles, such as leucocytes, from blood, for example, for subsequent analysis or even for treatment to insert a new gene, tag a radioactive label to the cell or other such procedure which involves removing leucocytes and then returning such modified cells to the whole organism or to an isolated organ or tissue. Such methods include multistep procedures involving sedimentation with dextran, followed by separation on density gradients. These procedures involve centrifugation, mixing, incubating and sometimes lysis of unwanted red blood cells. They take a number of hours to complete, involve skilled operatives and subject the cells to uncontrollable variables which may inadvertently affect their subsequent response to analytical procedures (Boynum, A. (1968) "Isolation of mononuclear cells and granulocytes from human blood". Scand. J. Clin. Lab. Invest. 21, Supple 97 (paper IV), 77–89). In addition the process has to be conducted in a laboratory and thus cannot be used in general medical or veterinary practice, at the bedside, in the field or in an out-patient clinic for example.

In response to the need for a rapid, simple and reliable method the following method was disclosed (Ferrante, A. and Thong, Y. H. (1980) "Optimal conditions for simultaneous purification of monocluclear and polymorphonuclear leucocytes from human peripheral blood by the Hypaque-Ficoll method". J. Immunol Methods, 35 109–117), which involved layering whole blood on to a mixture of Ficoll and sodium and/or meglumine diatrizoate prepared to specific densities, centrifuging the tube and collecting layers of leucocytes which were washed with centrifugation 2 to 3 more times. This 'improved' method which, enabled leucocytes to be separated, washed and-ready for analysis in about 1 to 2 hours still required a skilled operative and the need for a centrifuge. Also, it was not possible to carry out the procedure simultaneously on more than a very few samples (usually not more than 4). Furthermore, the method is not suitable for most bloods other than human, and does not work efficiently on blood from people having certain diseases, such as rheumatoid arthritis, juvenile rheumatoid arthritis or microcytic hypochromic anaemia. In addition, the method may fail or give variable results if the patient was receiving aspirin, indomethacin, prednisone, aurothioglucose, or drugs for the treatment of bronchial congestion, immunodeficiency anaemia or other diseases. An improved method, designed to enable leucocytes to be separated from these 'difficult' bloods was developed (Ferrante, A., James, E. W., Betts, W. J. and Cleland, L. G. (1982) "Rapid single step method for purification of polymorphonuclear leuocoytes from blood of patients with rheumatoid arthritis", Clin. exp. Immunol. 47, 749–752) in which the viscosity of the density medium was changed. The results of this improved method are still variable and not useful for quantifiable and comparative work.

The mode by which leucocytes are separated using density gradients in the prior art method is dependent upon the osmotic loss of water from sedimenting erythrocytes into a slightly hyperosmotic gradient medium. As the erythrocytes sediment and lose water this leads to a dilution of the Hypaque-Ficoll and subsequent production of a continuous gradient of lower density which the granulocytes enter at the exclusion of mononuclear cells and platelets. The production of the continuous gradient is dependent upon the erythocyte volume and usually requires about 5 ml blood to create a suitable gradient. A more recent improvement has been disclosed by Kalmar, J. R., Arnold R. R., Warbington, M. L. and Gardner, M. K. (1988) "Superior leukocyte separation with a discontinuous one-step Ficoll-Hypaque gradient for the isolation of human neutrophils", J. Immunol. Meth. 110, 275–281, in which one density medium of specific gravity 1.114 and osmolality of 458±10 mosM was used together with another medium of 1.077 specific gravity. The result was separation of leucocytes from 1 ml of whole blood.

In all the prior art methods, even the "improved" ones, the cells are subjected at times to adverse conditions. While it might be theoretically possible for a trained operative to work in precisely the same manner at each separation, the differences between the blood of various individuals especially during disease, make it impossible, in some instances, for the leucocytes to be separated from the erythrocytes. In addition, it is impracticable, even for trained operatives, to standardise the ways they perform the various manipulations involved in the lengthy procedure. The prior art methods are therefore only suited to the separation of leuococytes from whole normal blood and even then the sample volume required is not less than 1 ml.

Knight Scientific Limited, in EP-A-0489602, disclose a method by which leucocytes may be selectively removed from whole blood or any other biological fluid in which they occur by a rapid filtration technique using a filter material having a critical wetting surface tension greater than 53 dynes/cm and capable of holding said leucocytes by adsorption. The filter material together with the adsorbed leucocytes may then be subjected to a luminogenic material and introduced into a luminometer.

SUMMARY OF THE INVENTION

The present invention disclosed here bestows advantages over that described in EP-A-0489602. According to that document, the leucocytes remained adsorbed onto the filter and all subsequent analyses were carried out in the presence of the filter. In order to carry out replicate analyses, separate filtration devices are required and this increases the cost of the tests. Other determinations, such as tissue typing, histological analysis and other biochemical tests or the subsequent extraction from the leucocytes of enzymes and other substances including DNA and RNA is impeded by the presence of the filter.

The particles that may be adsorbed onto a filter in the prior art filtration technique are very small compared to the filter. In general, such particles have a diameter of up to 100 $\mu$m. Leucocytes are much smaller and have diameters of about 15 $\mu$m. Such small particles (i.e., having a diameter less than 100 $\mu$m) are known to behave very differently compared to larger objects, such as the filters which have a diameter of at least a few millimetres, when placed in a turbulent fluid. The present invention is based on our discovery that this difference can be exploited in a method according to which such particles may be separated from filters on which they are adsorbed.

The basis for the difference in behaviour of small particles compared to large objects in a liquid medium under flow may be explained with reference to the fact that the particles are of dimensions at which low Reynolds numbers dominate. Reynolds number is defined as:

$$Re = \rho UL/\mu$$

where $\rho$ is the density of the fluid, U is the velocity of flow past the object (or object through the fluid), L is some characteristic length of the object (usually the longest dimension parallel to the flow) and $\mu$ is the dynamic viscosity of the fluid. The Reynolds number is a pure number, without units, and its significance is relevant to the mechanism by which the adsorbed particles are liberated from the filter.

The Reynolds number approximates to the forces due to inertial effects relative to the forces that arise from the effects of viscosity. Knowledge of the Reynolds number thus allows one roughly to establish the kinds of forces which will dominate during flow.

As a rough generalization, the Reynolds number of an object is about 100 times the length or diameter of the object (in cm) times the speed of flow (cm/sec). At low Reynolds number 40 or less but generally 10 or less, inertial forces are small relative to viscous forces.

For objects of a given size and shape the Reynolds number is the same for a given fluid. However, if the dimensions of the objects are sufficiently different so that one object(s) has low Reynolds number(s) compared to the other, then the effect of turbulent flow on both objects will be different.

This situation is what prevails in the method herein described of liberating the adsorbed particles from the filter. The adsorbed particles are generally less than 100 $\mu$m in diameter, (the leucocytes are about 15 $\mu$m) and, therefore, move at low Reynolds number whereas the filter, is at least a few millimetres in diameter. At these dimensions, the effect of agitating the fluid so as to create turbulence and shear forces (in many directions) on the filter results in the filter moving relative to the particles. The particles are left in suspension as the filter, subjected to inertial forces, moves. Although the best results are obtained when turbulent flow prevails, the particles, unlike the filter, never experience turbulence and move smoothly in suspension in the liquid.

One object of the present invention is to provide a means of removing particles of low Reynolds numbers from a filter material to which they are retained by adsorption.

Another object of the present invention is to achieve the removal of adherent biological particles, such as leucocytes, from the filter in such a way that they are not damaged in the process and are not activated sooner than is required. A further object is to enable the rapid recovery of a sufficiently large proportion of biological particles in a medium in which other tests, especially those involving the addition of a luminogenic material, such as Pholasin (Registered Trade Mark), and the measurement of light emission in a luminometer, can be carried out.

The present invention provides a method of separating particles that move at low Reynolds number(s) from a filter material on which said particles are retained by adsorption which comprises locating the filter material having the adsorbed particles thereon in a liquid medium in a vessel, subjecting the filter material and the liquid to agitation of sufficient magnitude to create turbulence in the vessel thereby setting the liquid and filter material into turbulent motion and creating shear forces on the filter whereby the particles become suspended in the liquid and then separating the liquid containing the suspended particles from the filter material.

According to the present invention, there is also provided a method of recovering biological particles from a fluid in which the particles are present which comprises passing the fluid containing the particles through a filter material capable of selectively retaining the particles by adsorption whereby the particles are adsorbed onto and retained by the filter material, and separating the particles from the filter material according to the above method.

The method of the invention can be used to separate particles, of a size small enough to result in their moving at low Reynolds number, from filters onto which the said particles are adsorbed. The method can, for instance, be applied to the cleaning of filters to remove small particles, i.e., bacterial filters. Such a method may be combined with sonication, if required, and possibly coupled with intermittent back flushing of a small volume of liquid. However, the invention is particularly suitable for removing biological particles, such as leucocytes, from filters on which they are retained by adsorption and the invention will be further described with reference to the removal of biological particles.

By carrying out the method of the invention biological particles may be recovered in an undamaged state, i.e., in the same biochemical state as when they were first removed from the patient's body, in large numbers in an aqueous medium. The aqueous medium, containing the recovered particles, obtained by the present invention can be divided, if necessary, between separate tests and analyses thus precluding the need for further, separate filtrations. Furthermore, the method makes it possible to obtain a useful concentration of biological particles for testing from only a small volume of sample fluid, i.e., less than 1 ml. This is of particular importance when larger volumes of sample fluid are not available or cannot be taken from a patient's body without increasing the risk to the patient's health to an unacceptable level.

The method is useful for separating all biological particles, e.g., cellular matter, from a filter material to which the particles are bound by adsorption. The method has particular application in the separation of blood platelets and leucocytes since many testing and analytical procedures are carried out on these. Fluids, in which leucocytes may occur and from which they may be recovered, are listed above. According to a preferred embodiment, the invention provides a rapid means of recovering leucocytes from whole blood, human milk or semen thus enabling more rapid analysis and diagnosis for the patient.

The filter material in the method of the present invention will be one capable of selectively retaining the biological particles by adsorption when a fluid containing the said particles is passed or drawn through it. It may be comprised of one or more membranes of a suitable material or may have a fibrous or particulate composition. Preferably, the filter material will have a critical wetting surface tension greater than 53 dynes/cm. Filter materials useful in the present invention are known in the art.

There are a variety of devices that can be used to perform the simple separation of leucocytes from whole blood and the subsequent removal of the leucocytes from devices. They all embody a step in which the whole blood (or another fluid) is allowed to fall upon a filter one type of which is described in EP-A-0489602 and which has the ability selectively to retain leucocytes or platelets and allow the passage of erythrocytes or other non-adsorbed particles through the filter. The device might, for example, selectively remove leucocytes from milk or semen allowing non-adsorbed epithelial cells or sperm to pass through the filter.

Prior to passing the fluid containing the biological particles through the filter material, the filter material is preferably wetted to prepare the filter material for the filtration step, although satisfactory results can be obtained even if the filter is not washed. Typically, a physiological buffer is used to wet the filter material. This buffer may be heated to an elevated temperature prior to use, i.e., up to 40° C., although typically it will be at a temperature of about 37° C. The increased temperature will reduce the viscosity of the liquid, which has two effects. One is directly on the leucocytes, as they are more retentive at higher temperatures. The other is to increase the efficiency by which the red blood cells, also small enough to move at low Reynolds number, pass through the special filter. Filtration can be difficult at low Reynolds number with very high pressure drops across the filter and the reduction of viscosity during the filtration step increases the rate and efficiency of filtration. Filtration at a relatively high temperature is essential if the liquid to be filtered has a high fat content, such as raw milk or blood shortly after a meal. Preferably, the filter material is wetted with phosphate buffered saline (PBS), made up with: 0.8 g NaCl; 0.02 g KCl; 0.115 g $Na_2HPO_4 \cdot 2H_2O$; 0.02 g $KH_2PO_4$ per 100 ml solution. It is important, in the case where the fluid to be filtered is blood, that the PBS used to wet the filter does not contain any calcium or magnesium salts since the presence of calcium and magnesium on the filter may lead to clotting of the blood and may also accidentally lead to activation of the leucocytes. If the leucocytes become activated during the process of cell separation, then it is not possible subsequently to measure the activity of the leucocytes and relate such activity to various disease states.

Following any prior wetting step, the fluid containing the biological particles to be removed by adsorption on the filter material is delivered on to the filter material. Various techniques may be employed to deliver the fluid on to the filter material. Examples include the use of a syringe, pipette, automatic syringe and sampler, or delivery directly from the vein via a filter mounted within the blood collecting tube or syringe, or delivery from a tube or any other vessel into which the fluid has been temporarily stored prior to transfer to the filter.

The blood or other fluid can contain any anticoagulant, with EDTA being especially well suited to preventing the cells from becoming activated. Separation can be carried out from blood that does not contain any anticoagulant but for this procedure to be successful, the blood must not be allowed to stand for a time long enough for the clotting process to have developed sufficiently, significantly to impede the flow through the filter. Preferably, in the case where the fluid is blood this should be warmed, typically to at least 37° C., prior to delivery of the fluid to the filter material. We have found no difficulty in filtering routinely volumes of blood as small as 250 $\mu$l and have also obtained excellent results using only 50 $\mu$l.

The fluid may be drawn through the filter, for instance by way of a vacuum or pushed through the filter by direct pressure. Various devices can be made to hold one or a number of samples of fluid and the filtration step can be carried out manually or automatically, even controlled by a computer. As the fluid passes through the filter material, the biological particles of interest, such as leucocytes, become adsorbed on to the filter material and, thereby, become retained thereon. The non-adsorbed components of the fluid pass through the filter material and may be collected for eventual disposal in a container. The container may be an absorbent pad as described in EP-A-0489602 although, preferably, is a closable vessel to enable safe disposal without contamination or leakage of the contents.

Following the first filtration step, which is completed in a few seconds, the filter material together with the adsorbed biological particles is preferably washed with a physiological buffer, such as a phosphate buffered saline containing no calcium or magnesium ions but to which albumin at a concentration of 0.1% may have been added to good effect. This washing buffer may be preheated to an elevated temperature which will be pre-selected depending upon the differential adsorption of the types of biological particles, e.g., leucocytes, during the step in which they are removed from the filter. In a typical embodiment, the washing buffer will be preheated to a temperature of about 37° C. The volume of washing buffer used in the washing step will, in general, be from 1 to 6 times, preferably about four times, the volume of the fluid subjected to filtration. Essential to the procedure to ensure quiescence of leucocytes and to prevent clotting is the absence of calcium and magnesium salts from the washing buffer.

The filter material having biological particles adsorbed thereon is, according to the present invention, placed in a liquid medium which is typically aqueous and preferably sterile and is subjected to agitation of sufficient magnitude to create turbulence in the tube, or other vessel, setting the liquid and filter into turbulent or random motion and thus creating shear forces, in many directions, on the filter whilst leaving the particles, not affected by the turbulent flow, in suspension in the liquid and then separating the liquid with liberated particles, from the filter. The liquid, preferably aqueous, will usually be contained in a receptacle and the filter material having adsorbed particles will be transferred from the filter apparatus to the receptacle and, thus, brought into contact with the liquid medium in which particle removal from the filter material will be effected. The aqueous medium is, typically, a physiological buffer such as phosphate buffered saline. The temperature of this medium when it contacts the filter material may generally be from 0° C. to about 40° C. However, we have found that the removal of the biological particles from the filter material is facilitated by locating the filter material in an aqueous medium having a low temperature. Preferably, then, the temperature of the aqueous medium, when it contacts the filter material and adsorbed particles, will be less than 10° C., preferably from 1° C. to 8° C., especially about 4° C. Reducing the temperature has the effect of increasing the viscosity of the liquid medium and thus reducing the Reynolds number further.

The presence, in the aqueous medium, of a substance which counters adhesion between the particles, i.e., reduces the capacity of the biological particles to adhere together, has been found to improve the removal of the particles from the filter material. Examples of such anti-adhesion agents include, but are not limited to, heparin, gelatin and albumin. A satisfactory concentration of heparin is 5 units $ml^{-1}$. Gelatin of low bloom (about 75 bloom) gives good results. The amounts of anti-adhesion agents, gelatin and albumin present in the aqueous medium is typically from 0.01 to 0.7% by weight, although good results have been achieved using about 0.1% by weight of the agent. These anti-adhesion agents may also increase the viscosity of the liquid medium and, thus, reduce the Reynolds number of the particles.

If the adsorption of the particles on the filter is in part, or totally, dependent upon electrostatic charges or other interactions, i.e., hydrophobic interactions, then removal of the particles in the process described above may be enhanced by the inclusion of substances, such as zwitterions, to neutralise charge effects or in the case of hydrophobic interactions, reduce the salt content of the buffer to reduce the affinity. In some instances, the particles may have a coating which takes on a positive or negative charge at different values of pH. If the filter material is coated with a substance that results in a charge then the particles may be made to adhere to the filter by filtering in the presence of a buffer which creates charge on the particles opposite to that on the filter. Changing the pH, of the removing buffer to a value of pH that either results in no charge on the particle or reverses the charge so that the particles now have the same charge as the filter, may improve the efficiency of removal of the particles on agitation.

The volume of the aqueous medium contacted with the filter medium and adsorbed particles in the receptacle will, in general, be from 1 to 10 times the volume of the fluid filtered in the first instance.

To effect removal, or de-adsorption, of the biological particles from the filter material the filter material with the adsorbed particles, which is located in the aqueous medium, is subjected to agitation of sufficient magnitude to create turbulence and shear forces (in many directions) on the filter resulting in the filter moving relative to the particles. The particles are left in suspension as the filter, subjected to inertial forces, moves relative to the particles. Various means of agitating the filter to attain sufficient turbulence to produce shearing forces in many directions on the filter are known. One such means is a vortex mixer. For example, the filter may be placed into 500 μl removing buffer contained in a small tube that can be conical, rounded or even flat at the bottom. A commercially available vortex mixer involves a rubber cup into which a tube is placed. The cup revolves in an eccentric orbit of small radius. A tube containing a liquid is pressed into this cup; the tube is not allowed to spin but the contents within the tube spin and a vortex is created. However, creation of a vortex of liquid is not essential for the successful removal of cells adsorbed on the filter; if sufficient agitation is created so that the filter moves in a turbulent manner then the cells will also be removed. As the filter spins or moves in a turbulent manner, the cells are liberated during the agitation. The cells that were adsorbed onto the filter are less than 100 μm in diameter (with leucocytes having an average diameter of 15 μm). For such small particles, inertia plays an insignificant role in their motion which is directed by forces acting upon them at a particular moment and not by anything in the immediate past. Such particles are said to move at low Reynolds number (a dimension-less number which is the ratio of inertial to viscous forces acting upon the particles). The filter, however is of a dimension in which inertia plays an important role in its motion. Therefore when the filter and the adsorbed leucocytes or biological particles are subjected to this eccentric agitation the cells are left in suspension while the filter upon which they had been adsorbed is subjected to inertia and moves relative to the particles. Another way would be to subject the tube and its content to a vibrational frequency of the order of 50 Hertz from mains electricity. Such a vibrational frequency is attained by an electric razor. Similarly vibration of a similar frequency can be obtained with a make and break circuit device from a DC supply. There are a number of other ways to create turbulence and shear forces on the filter one of these is to rapidly oscillate the tube back and forth.

A yet further way of bringing about the separation of particles from a filter material on which they are retained by adsorption is by subjecting the filter material, in a suitable vessel and in the presence of aqueous liquid, to agitation created by the movement towards and away from the filter material in the vessel of an agitation means, for example a plunger or piston-like device. For instance, the filter material and aqueous liquid may be located in a tubular vessel and the agitation means may take the form of a tube, e.g., formed of plastics material, having an external diameter which is smaller than the internal diameter of the tubular vessel which plastics tube has a closed bottom end. By moving the agitation means, such as by manual operation, inside the tubular vessel with alternating motion towards and away from the filter material with particles adsorbed thereon, the filter material is subjected to turbulence and to shear forces which cause the particles to become desorbed from the filter material and become suspended in the aqueous liquid in the tubular vessel. In one embodiment, the closed bottom end of the plastics tube is a flat perforated plate or is formed from a woven or non-woven fabric which is pervious to the aqueous liquid but which does not adsorb the particles so that the aqueous liquid may pass through the end of the plastics tube as this is moved into and out of the tubular vessel. According to another embodiment, the agitation means comprises a flat member which is attached to a rod. The flat member may be formed of a perforated plastics plate or a plate of another suitable perforated material or comprises a flat frame retaining or partially covered by one or more pieces of a mesh or woven or non-woven fabric of appropriate pore size to allow the passage therethrough of newly suspended particles in the aqueous liquid but not the filter material on to which the particles are initially adsorbed. The mesh or woven or non-woven fabric which is pervious to the aqueous liquid and the separated particles will not have the ability to retain the particles by adsorption. The rod may be removably attached to the flat member, e.g., by screw thread means, and may thus be removed from the member when the separation of the particles from the filter material is complete. The member, thus, remains in the vessel resting on the filter material so allowing the use of the liquid containing the suspended particles without interference from the filter material.

According to the above-described procedures, biological particles are released into the aqueous medium which can be decanted from, or otherwise separated from, the filter material. The filter material may then be located into another fresh supply of aqueous medium and the procedure repeated so as to remove any further particles from the filter material. These further particles may comprise the same as, or a different sub-set of particles compared to, the first particles released from the filter material. When the filter material is sufficiently depleted of most or all of the adsorbed biological particles it may be discarded. The different extracts containing the de-adsorbed particles may be pooled or retained separately.

A small volume (e.g., 10%, 100 $\mu$l in a total volume of 1 ml) of concentrated calcium and magnesium salts (0.1 g anhydrous $CaCl_2$; 0.1 g $MgCl_2 \cdot 6H_2O$ per 100 ml solution) may be added to the particles removed from the filter to restore the ions needed by the cells to respond normally to stimuli of the kind used in various cell activation studies. Alternatively, calcium and magnesium salts at normal physiological concentrations can be included in the removing buffer although the absence of the salts during all the separation procedures prevents the cells from becoming inadvertently activated.

The entire procedure can be completed in less than 1 minute and devices may be designed to carry out the separation simultaneously on a number of different samples. The separated particles can now be used in any way desired. An example of a method that works exceptionally well is the transfer of 100 $\mu$l aliquots of separated cells into cuvettes containing 250 $\mu$l of a solution of Pholasin® in physiological buffer plus an additional 100 $\mu$l of either buffer or drug. The preparation is placed in a luminometer and an effector, a stimulating agent such as phorbol myristate acetate, is injected into the cuvette and light measured as the leucocytes become activated.

The separated leucocytes can even be tagged with, say, a radioactive label, and introduced into an organism or excised organ or tissue. If such a procedure is undertaken then the separation must be carried out under sterile conditions and the buffers and device are to be supplied sterile.

DESCRIPTION OF THE DRAWINGS

The invention will be further described with references to the accompanying drawings of which.

DETAILED DISCUSSION OF PREFERRED EMBODIMENTS

Figure 1A:
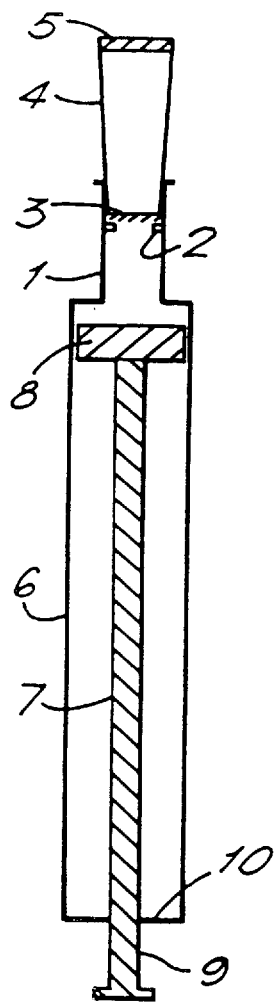
FIGS. 1A–1C show the device in its initial configuration before filtration of a fluid has commenced.
Figure 1B:
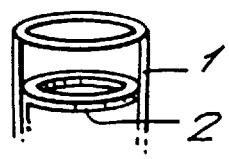
Figure 1C:
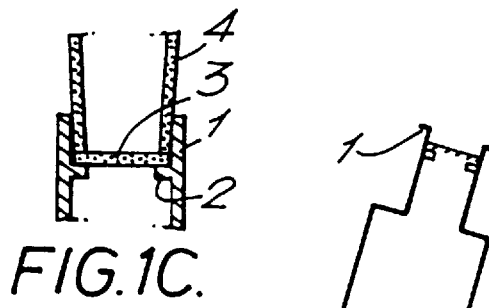

In FIGS. 1A–1C the device comprises a tube 1 having a ledge 2 running around the inner surface of the tube on which a filter 3 rests. Alternatively, the tube may be fitted with a perforated plate on which sits a removable filter 3. The filter has a diameter equal to the diameter of the plate. A funnel-shaped receptacle 4, which may be closed by an openable cap 5, is attached to the tube for instance by means of a screw thread provided at the bottom of the receptacle which engages with a complimentary thread provided at the top of the tube or which may be a push fit within tube 1. Other forms of attaching the receptacle to the tube are also possible, as is known in the art. The size of the filter is such that it is held in position by the receptacle when attached to the tube.

More than one filter can be employed, for instance to collect different types of biological particles on different filters, as is known in the art. The filter or filters are typically circular although other shapes, e.g., elliptical, square or rectangular may be used. The tube opens out into a barrel 6 which is provided with a plunger 7 slidably disposed therein. The plunger has a head 8 which makes an air-tight and fluid-tight seal with the internal sides of the barrel and a handle 9 which extends through the end of the barrel 10.

In use, fluid containing the biological particles to be recovered, e.g., blood, is added to the receptacle 4 and is drawn through the filter 3 using the suction caused by withdrawing the plunger 7 in the barrel 6. While the biological particles are adsorbed on and, thus, retained by the filter, the non-adsorbed portion of the fluid including particles of similar size to those retained, such as the red blood cells, is collected in the barrel 6. Following the filtration, a quantity of a washing buffer is added to the receptacle 4 and this is also drawn through the filter by further withdrawal of the plunger from the barrel.

Figure 2:
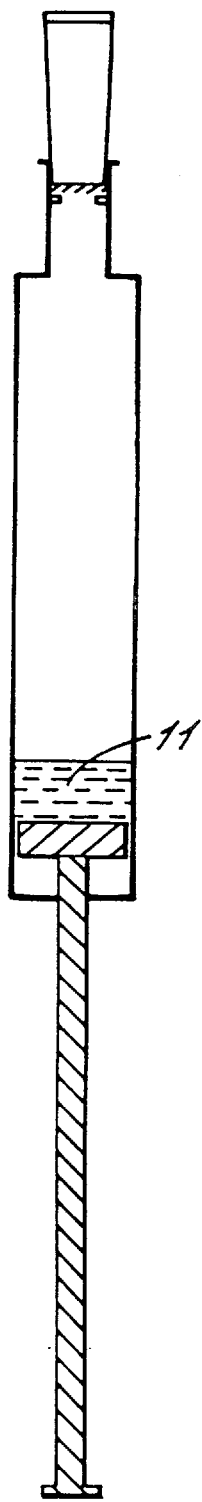
FIG. 2 shows the same device after filtration.

After the washing stage has been completed, the device will have the configuration shown in FIG. 2 wherein the washing buffer and the non-adsorbed portion of the fluid 11 is retained in the barrel.

Figure 3A:
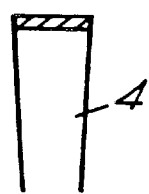
FIGS. 3A–3C show the device disassembled after filtration to release the filter material.
Figure 3B:
Figure 3C:
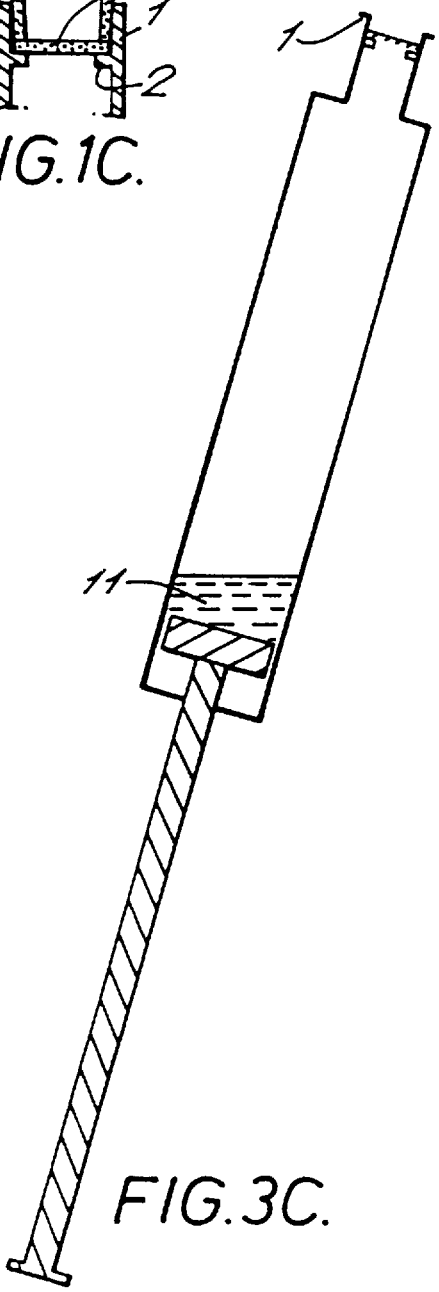

Then, the receptacle 4 is disengaged from the tube 1, as shown in FIG. 3A. The filter 3 now with adsorbed biological particles thereon is thus released and may then be placed in contact with an aqueous medium in a receptacle for the recovery of the particles (not shown). The barrel portion of the device containing the non-adsorbed fluid and washings may then be disposed of safely without spillage of any of the contents.

The tube end of the barrel may be closed with a cap or lid (not shown) to ensure the security of the contents in the barrel. By disposing of the contents of the barrel in this way, the release of any pathogens or infectious agents that may be present in the fluid is prevented.

By an appropriate modification of the device shown in FIG. 1, it will be seen that it is possible to deliver blood direct from a patient's vein to the filter for instance by adapting the receptacle to receive a hypodermic needle. The blood may, in such a case, be delivered to the filter by venous pressure or by withdrawing it from the vein using the plunger in the barrel.

This new invention also embodies the safe collection of waste blood products which can be carried out in a number of different ways. In the manual method, handling of blood or other fluids containing leucocytes is kept to an absolute minimum whereas with the automated version the operator is spared any contact with the whole blood or its washings as the entire procedure is carried out automatically.

The device can also be adapted to use the collected filtrate, for example in the ease of sperm separated from contaminating leucocytes when the sperm can be used in other tests, in particular those designed to test the sperm cells in fertility tests. The interpretation of such tests is frequently hindered by contaminating leucocytes in the preparation, and this device can be used to produce a pure preparation of such particles.

Figure 4A:
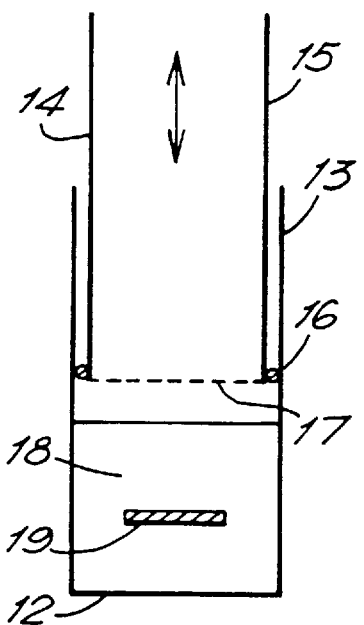
FIGS. 4A–4C show a preferred embodiment of an apparatus suitable for carrying out the method of the invention.
Figure 4B:
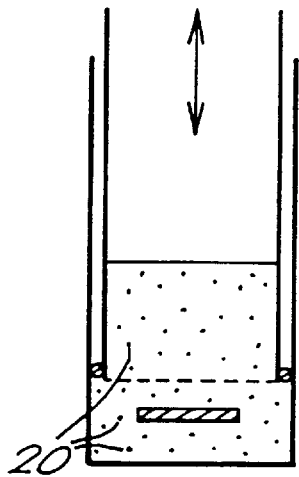
Figure 4C:
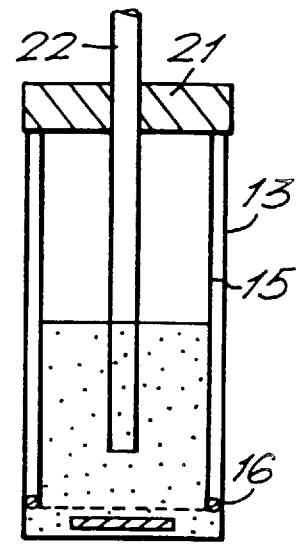

One preferred embodiment of an apparatus which is suitable for performing the method of the invention is illustrated schematically in FIG. 4. According to this, the apparatus is formed of a vessel 12 which comprises a first tube 13 and an agitation means 14 comprising a second tube 15 which has an external diameter smaller than the internal diameter of the first tube. The second tube 15 of smaller diameter is fitted with an O ring 16 to facilitate ease of motion of the smaller tube within the larger tube while preventing liquid from leaking from the first tube during operation. According to an alternative embodiment (not illustrated) the second tube may just touch the inner walls of the first tube and the material from which it is made permits easy movement of the second tube within the first tube. Both the first tube and the second tube are typically formed of plastics material. The second tube has a bottom end 17 which is perforated. Alternatively, the end of the second tube may be closed by a piece of mesh or woven or non-woven fabric pervious to the liquid, such as a filter material. In such cases, care should be taken, however, to choose a fabric that has no adsorptive properties related to the particles to be separated according to the method of the present invention. To operate the apparatus shown in FIG. 4 to carry out the method, an appropriate quantity of liquid medium 18 and a filter material 19 having particles retained thereon by adsorption are added to the vessel. It is possible to use more than one filter material having adsorbed particles so as to produce a more concentrated final suspension. The agitation means is then inserted into the vessel and is moved alternatively towards and away from the bottom of the vessel (as shown by the direction of the arrows in FIGS. 4A and 4B) so that, as it moves towards the bottom of the vessel, the liquid passes through the perforations in the bottom of the second tube and thus, enters the second tube. The reciprocating motion of the agitation means creates turbulence in the liquid and shear forces which act on the filter material so as to separate the particles 20 therefrom. The thus-liberated particles 20 become suspended in the liquid in the vessel which liquid, as described above, is drawn through the pervious end of the second tube. When the reciprocating motion of the agitation means has been carried out for a suitable period of time such that separation of the particles from the filter material is complete the agitation means may be used as shown in FIG. 4C to retain the depleted filter material at the bottom of the vessel to facilitate the removal and use of the liquid medium containing the suspended particles.

According to the preferred embodiment shown in FIG. 4C, both tubes, i.e., first tube 13 and the pushed down second tube 15, are sealed with a removable cap 21 through which is inserted tubing 22 to enable the dispensing of the suspension of particles.

Figure 5:
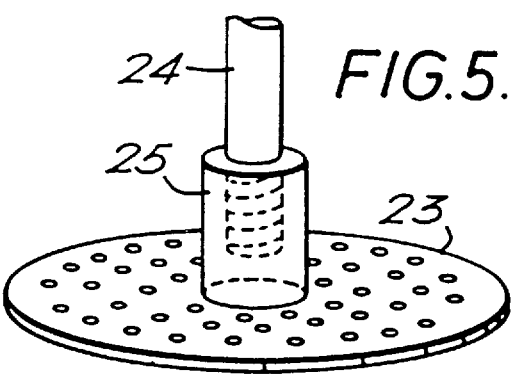
FIGS. 5 and 6 show alternative agitation means that may be used in the apparatus illustrated in FIG. 4A.
Figure 6:
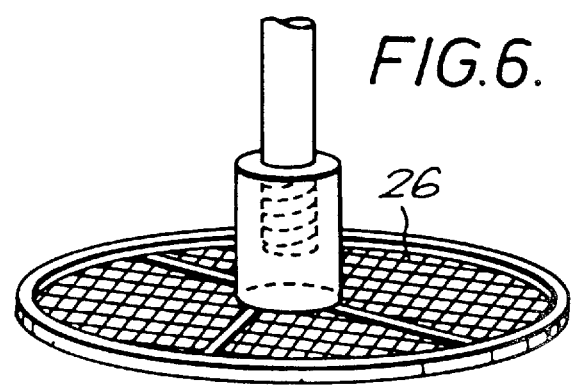

Instead of using the agitation means as shown in FIG. 4, use may be made of the alternative agitation means illustrated in FIG. 5 or FIG. 6. The agitation means shown in FIG. 5 comprises a perforated plate 23 typically formed of a plastics material. The plate is centrally attached to a rod 24. The rod has an end which is screw threaded and which is adapted to engage with an internally threaded block 25 attached to the plate. After separation of the particles, the rod may be unscrewed to leave the plate in the vessel to retain the filter material. Instead of a perforated plate, a mesh or fabric-covered frame 26, as shown in FIG. 6, can be used in the agitation means.

EXAMPLE

A suitable filter was positioned in a device of the type illustrated in FIG. 1 and described above.

250 µl of warm (37° C.) washing buffer was drawn through the filter to wet and warm the filter. The whole device can also be kept warm. Then 250 µl warm blood (37° C.) was allowed in impinge onto the filter and the blood was drawn through the filter as described previously. 1 ml of warm washing buffer was then drawn through the filter.

The filter was then removed from the support and placed in a small centrifuge tube (maximum capacity 1.5 ml) containing 500 µl cold removing buffer. The tube was subjected to four×5 second bursts of eccentric agitation at fixed speed 2 on a vortex mixer (Autovortex mixer SA2 Stuart Scientific).

The liquid containing the liberated leucocytes were removed from the tube using a pipette. Then, 500 µl of removing buffer were added to the tube containing the filter and the tube was subjected to two×5 second bursts of eccentric agitation at fixed speed 2 on the vortex mixer. The liquid was removed from the tube by pipette and combined with the liquid recovered from the first treatment. The total volume of liquid recovered was between 900–950 µl. From a leucocyte count it was determined that up to about 90% of the particles retained from the whole blood during the filtration process could be recovered.

We claim:

1. A method of separating particles that move at a Reynolds number no greater than 40 from a filter material on which said particles are retained by adsorption which method comprises the steps of:

locating the filter material having the adsorbed particles thereon in a liquid medium in a vessel;

subjecting the filter material and the liquid to agitation of sufficient magnitude to create turbulence in the vessel thereby setting the liquid and filter material into turbulent motion and creating shear forces on the filter whereby the particles become suspended in the liquid; and separating the liquid containing the suspended particles from the filter material.

2. A method of separating particles that move at a Reynolds number no greater than 40 from a filter material on which said particles are retained by adsorption, which method comprises the steps of:

locating the filter material having the adsorbed particles thereon in a liquid medium in a vessel;

subjecting the filter material and the liquid to agitation of sufficient magnitude to create turbulence in the vessel thereby setting the liquid and filter material into turbulent motion and creating shear forces on the filter whereby the particles become suspended in the liquid; and separating the liquid containing the suspended particles from the filter material wherein the particles are one of leucocytes and blood platelets.

3. A method of separating particles that move at a Reynolds number no greater than 40 from a filter material on which said particles are retained by adsorption, which method comprises the steps of:

locating the filter material having the adsorbed particles thereon in a liquid medium in a vessel;

subjecting the filter material and the liquid to agitation of sufficient magnitude to create turbulence in the vessel thereby setting the liquid and filter material into turbulent motion and creating shear forces on the filter whereby the particles become suspended in the liquid; and separating the liquid containing the suspended particles from the filter material, wherein the liquid medium is a phosphate buffered saline.

4. A method according to claim 3, wherein the phosphate buffered saline also contains an anti-adhesion agent to reduce the capacity of the particles to adhere together.

5. A method according to claim 4, wherein the anti-adhesion agent is selected from gelatin, albumin and heparin.

6. A method according to claim 3, wherein the phosphate buffered saline also contains one of calcium and magnesium at a physical concentration.

7. A method as claimed in claim 1, wherein the filter material on which the particles are retained by adsorption and the liquid medium are subjected to agitation in the vessel by movement of an agitation means towards and away from the filter material.

8. A method according to claim 7, wherein the agitation means comprises a tube having a closed bottom end.

9. A method of separating particles that move at a Reynolds number no greater than 40 from a filter material on which said particles are retained by adsorption, which method comprises the steps of:

locating the filter material having the adsorbed particles thereon in a liquid medium in a vessel;

subjecting the filter material and the liquid to agitation of sufficient magnitude to create turbulence in the vessel thereby setting the liquid and filter material into turbulent motion and creating shear forces on the filter whereby the particles become suspended in the liquid; and separating the liquid containing the suspended particles from the filter material wherein the filter material on which the particles are retained by adsorption and the liquid medium are subjected to agitation in the vessel by movement of an agitation means towards and away from the filter material, said agitation means comprises a tube having a closed bottom end, wherein the closed bottom end of the tube is formed of one of a perforated plate, a woven fabric and a non-woven fabric.

10. A method of separating particles that move at a Reynolds number no greater than 40 from a filter material on which said particles are retained by adsorption, which method comprises the steps of:

locating the filter material having the adsorbed particles thereon in a liquid medium in a vessel;

subjecting the filter material and the liquid to agitation of sufficient magnitude to create turbulence in the vessel thereby setting the liquid and filter material into turbulent motion and creating shear forces on the filter whereby the particles become suspended in the liquid; and separating the liquid containing the suspended particles from the filter material, wherein the filter material on which the particles are retained by adsorption and the liquid medium are subjected to agitation in the vessel by movement of an agitation means towards and away from the filter material, said agitation means comprises a flat member centrally attached to a rod.

11. A method according to claim 10, wherein the rod is removable from the flat member.

12. A method according to claim 10 or 11, wherein the flat member is a perforated plate.

13. A method according to either claim 10 or 11, wherein the flat member comprises a flat frame which is at least partially covered with a mesh or woven or non-woven fabric.

14. A method of recovering biological particles from a fluid in which the particles are present which method comprises the steps of:

passing the fluid containing the particles through a filter material capable of selectively retaining the particles by adsorption whereby the particles are adsorbed onto and retained by the filter material; and separating the biological particles that move at a Reynolds number not greater than 40 from the filter material by:

locating the filter material having the adsorbed particles thereon in a fluid in a vessel;

subjecting the filter material and the fluid to agitation of sufficient magnitude to create turbulence in the vessel thereby setting the liquid and filter material into turbulent motion and creating shear forces on the filter whereby the particles become suspended in the fluid; and separating the fluid containing the suspended particles from the filter material.

15. A method according to claim 14, wherein prior to passing the fluid containing the particles through the filter material the filter material is wetted with a physiological buffer at 37° C. which contains no calcium or magnesium ions.

16. A method according to claim 14, wherein the fluid containing the biological particles is blood at a temperature of about 37° C.

17. A method according to claim 14, wherein, following the filtration step, a washing buffer medium which contains no calcium or magnesium ions at about 37° C. is passed through the filter material.

18. A method according to claim 14, wherein the filter material having the biological particles retained thereon by adsorption is transferred to a receptacle containing an aqueous medium at a temperature of less than 10° C.

19. A method according to claim 18, wherein the temperature of the aqueous medium is in the range of from 1° C. to 8° C.

20. A method according to claim 19, wherein the aqueous medium has a temperature of about 4° C.

21. A method according to claim 14, wherein the filter material is located in a syringe having on one side of the filter material a barrel provided with a plunger slidably disposed therein and on the other side of the filter material a receptacle for the fluid containing the biological particles and wherein the fluid is drawn from the receptacle, through the filter material and into the barrel by the withdrawal of the plunger.

22. A method according to claim 21, wherein the receptacle is connected to a tube inserted into a human or non-human patient's body and the fluid is delivered, to the filter material direct from the patient's body.

23. A method according to claim 22, wherein the fluid is blood and the receptacle is connected to a tube inserted into the patient's vein.

24. An apparatus for separating particles that move at a Reynolds number of no greater than 40, said apparatus comprising:

a vessel containing a filter material on which said particles are retained by adsorption;

a liquid medium; and agitation means for agitating the contents of the vessel by movement towards and away from one end of the vessel so as to create sufficient turbulence and shear forces on the filter whereby said particles become suspended in the liquid.

25. An apparatus for separating particles that move at a Reynolds number of no greater than 40, said apparatus comprising:

a vessel containing a filter material on which said particles are retained by adsorption;

a liquid medium; and agitation means for agitating the contents of the vessel by movement towards and away from one end of the vessel so as to create sufficient turbulence and shear forces on the filter whereby said particles become suspended in the liquid, wherein the vessel comprises a first tube and wherein the agitation means comprises a second tube having an external diameter smaller than an internal diameter of the first tube and wherein the second tube has a closed end.

26. An apparatus according to claim 25, wherein the closed end of the second tube which forms the agitation means is pervious to the liquid medium.

27. An apparatus for separating particles that move at a Reynolds number of no greater than 40, said apparatus comprising:

a vessel containing a filter material on which said particles are retained by adsorption;

a liquid medium; and agitation means for agitating the contents of the vessel by movement towards and away from one end of the vessel so as to create sufficient turbulence and shear forces on the filter whereby said particles become suspended in the liquid, wherein the agitation means comprises a flat member centrally attached to a rod.

28. An apparatus according to claim 27, wherein the rod is removable from the flat member.

29. An apparatus according to claim 27, wherein the flat member is a perforated plate or comprises a flat frame retaining or at least partially covered by one or more pieces of a mesh or a woven or non-woven fabric pervious to the liquid medium.

30. An apparatus for separating particles that move at a Reynolds number of no greater than 40, said apparatus comprising:

a vessel containing a filter material on which said particles are retained by adsorption;

a liquid medium; and at least one agitator moving towards and away from one end of the vessel thereby agitating the contents of the vessel so as to create sufficient turbulence and shear forces on the filter whereby said particles become suspended in the liquid.

* * * * *